US009224240B2

(12) United States Patent
Lazebnik

(10) Patent No.: US 9,224,240 B2
(45) Date of Patent: Dec. 29, 2015

(54) DEPTH-BASED INFORMATION LAYERING IN MEDICAL DIAGNOSTIC ULTRASOUND

(75) Inventor: Roee Lazebnik, San Jose, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 932 days.

(21) Appl. No.: 12/953,265

(22) Filed: Nov. 23, 2010

(65) Prior Publication Data

US 2012/0128221 A1   May 24, 2012

(51) Int. Cl.
| | | |
|---|---|---|
| G06T 17/00 | (2006.01) | |
| A61B 8/00 | (2006.01) | |
| G06T 19/00 | (2011.01) | |
| A61B 8/08 | (2006.01) | |

(52) U.S. Cl.
CPC ................. *G06T 17/00* (2013.01); *A61B 8/463* (2013.01); *A61B 8/466* (2013.01); *A61B 8/485* (2013.01); *G06T 19/00* (2013.01); *A61B 8/483* (2013.01); *G06T 2210/41* (2013.01)

(58) Field of Classification Search
None
See application file for complete search history.

(56) References Cited

U.S. PATENT DOCUMENTS

| | | | | |
|---|---|---|---|---|
| 5,251,635 | A * | 10/1993 | Dumoulin et al. | 600/417 |
| 5,488,952 | A * | 2/1996 | Schoolman | 600/443 |
| 5,493,595 | A * | 2/1996 | Schoolman | 378/41 |
| 6,014,473 | A * | 1/2000 | Hossack et al. | 382/294 |
| 6,041,140 | A * | 3/2000 | Binns et al. | 382/209 |
| 6,181,768 | B1 * | 1/2001 | Berliner | 378/41 |
| 6,817,982 | B2 * | 11/2004 | Fritz et al. | 600/443 |
| 7,837,624 | B1 * | 11/2010 | Hossack et al. | 600/443 |
| 7,876,947 | B2 * | 1/2011 | Lee et al. | 382/131 |
| 8,096,947 | B2 * | 1/2012 | Salgo et al. | 600/437 |
| 8,180,016 | B2 * | 5/2012 | Kanno | 378/5 |
| 8,565,505 | B2 * | 10/2013 | Bergmans et al. | 382/131 |
| 8,878,912 | B2 * | 11/2014 | Raveendran et al. | 348/51 |
| 2003/0097068 | A1 * | 5/2003 | Hossack et al. | 600/443 |
| 2004/0155659 | A1 * | 8/2004 | Prado | 324/322 |
| 2005/0033173 | A1 * | 2/2005 | Von Behren et al. | 600/443 |
| 2005/0047636 | A1 * | 3/2005 | Gines et al. | 382/131 |
| 2005/0078861 | A1 * | 4/2005 | Usikov | 382/131 |
| 2005/0231504 | A1 * | 10/2005 | Heng et al. | 345/420 |
| 2006/0092172 | A1 * | 5/2006 | Tung et al. | 345/596 |
| 2006/0129361 | A1 * | 6/2006 | Miura et al. | 703/2 |
| 2006/0164411 | A1 * | 7/2006 | Lee | 345/419 |
| 2006/0173338 | A1 * | 8/2006 | Ma et al. | 600/456 |
| 2007/0076016 | A1 * | 4/2007 | Agarwala et al. | 345/629 |

(Continued)

OTHER PUBLICATIONS

Gibbs et al. "Chapter Ultrasound Beam Shape" www.isradiology. org/isr/docs_books/basic/Chapter5.pdf pp. 1-9.*

(Continued)

*Primary Examiner* — Chan Park
*Assistant Examiner* — Mia M Thomas

(57) ABSTRACT

Information layering is provided in medical imaging. Two or more types of information are provided in one image. A three-dimensional surface is formed for two-dimensional scanning and/or imaging. The depth or third dimension is mapped to one type of data. Variation in values of this type of data causes variation in the surface away from flat. Data of another type is mapped to the surface, such that each location having a color or gray scale value based on the other type and a depth based on the one type. The surface is rendered using three-dimensional rendering to show the depth information even though both types of data represent a scanned plane. Stereoscopic viewing may allow the user to better visualize the depth information.

18 Claims, 2 Drawing Sheets

(56) References Cited

U.S. PATENT DOCUMENTS

| | | | |
|---|---|---|---|
| 2007/0122027 A1* | 5/2007 | Kunita et al. | 382/154 |
| 2007/0229500 A1* | 10/2007 | Engel et al. | 345/422 |
| 2008/0193002 A1* | 8/2008 | Ying et al. | 382/131 |
| 2008/0253627 A1* | 10/2008 | Boyden et al. | 382/128 |
| 2008/0269611 A1* | 10/2008 | Pedrizzetti et al. | 600/454 |
| 2009/0018808 A1* | 1/2009 | Bronstein et al. | 703/11 |
| 2009/0103791 A1* | 4/2009 | Suri et al. | 382/131 |
| 2009/0128553 A1* | 5/2009 | Perry et al. | 345/419 |
| 2009/0136109 A1* | 5/2009 | Salgo et al. | 382/131 |
| 2009/0257551 A1* | 10/2009 | Dafni et al. | 378/6 |
| 2010/0017171 A1* | 1/2010 | Spilker et al. | 703/2 |
| 2010/0074503 A1* | 3/2010 | Bruder et al. | 382/131 |
| 2010/0092038 A1* | 4/2010 | Theodore et al. | 382/103 |
| 2010/0310040 A1* | 12/2010 | Hsieh et al. | 378/17 |
| 2010/0310141 A1* | 12/2010 | Wilson | 382/131 |
| 2011/0228976 A1* | 9/2011 | Fitzgibbon et al. | 382/103 |
| 2011/0273528 A1* | 11/2011 | Sazawa | 348/36 |
| 2012/0013607 A1* | 1/2012 | Lee | 345/419 |
| 2012/0120368 A1* | 5/2012 | Fujimora et al. | 351/206 |
| 2012/0281873 A1* | 11/2012 | Brown et al. | 382/103 |
| 2013/0294665 A1* | 11/2013 | Rao et al. | 382/131 |
| 2013/0294666 A1* | 11/2013 | Bultema | 382/131 |
| 2014/0044347 A1* | 2/2014 | Sato | 382/154 |
| 2015/0002490 A1* | 1/2015 | Han et al. | 345/204 |

OTHER PUBLICATIONS

Yao et al. "Non-Rigid Registration and Correspodence Finding in Medical Image Analysis Using Multiple-Layer Flexible Mesh Template Matching" International Journal Pattern Recognition and Artificial Intelligence (IJPRAI) vol. 17, No. 7 (2003) pp. 1-21.*

Uhlendorf et al. "Nonlinear Acoustical Response of Coated Microbubbles in Diagnostic Ultrasound" 1994 Ultrasound Symposium (IEEE) pp. 1-4.*

Song et al. "3D Mesh and Multi-View Synthesis Implementation Using Stereo Cameras and a Depth Camera" IEEE (2013) pp. 1-3.*

* cited by examiner

DEPTH-BASED INFORMATION LAYERING IN MEDICAL DIAGNOSTIC ULTRASOUND

BACKGROUND

The present embodiments relate to simultaneous viewing of different types of information. Ultrasound imaging allows users to visualize several layers of data. For example, Doppler data may be superimposed on a B-mode image using color. The B-mode information is presented in gray scale with echogenic tissue as bright pixels and hypoechoic structures as dark pixels. Simultaneously, color is assigned to represent velocity of flow through each anatomical location, for example using red to indicate flow towards the transducer and blue for flow away from the transducer. Using this technique, two types of data (echogenicity and flow) are simultaneously visualized in one image. Similar approaches are feasible for three dimensional data. However, presentation of additional information may be confusing.

There are clinically relevant scenarios where more than two types of data are simultaneously visualized. For example, in preparation for a biopsy, a user may want to visualize B-mode, Doppler, and elastographic information in order to plan a path for instrument travel to a target. To allow for the additional information, separate images are displayed side by side. While practical, this method may have disadvantages, including a reduction of the physical size of a given image to fit both images on the display and/or requiring the user to approximate the spatial relationship of structures in separate images based on their locations within the images. The same anatomical location may appear quite different using B-mode versus elastographic scanning, requiring the user to mentally register these structures relative to the image boundaries.

BRIEF SUMMARY

By way of introduction, the preferred embodiments described below include a method, system, instructions, and computer readable media for information layering in medical imaging. Two or more types of information are provided in one image. A three-dimensional surface is formed for two-dimensional scanning and/or imaging. The depth or third dimension is mapped to one type of data. Variation in values of this type of data causes variation in the surface away from flat. Data of another type is mapped to the surface, such that each location has a color or gray scale value based on the other type and a depth based on the one type. The surface is rendered using three-dimensional rendering to show the depth information even though both types of data represent a scanned plane. Stereoscopic viewing may allow the user to better visualize the depth information.

In a first aspect, a method is provided for information layering in medical diagnostic ultrasound. At least first and second types of data both representing different types of characteristics of a planar region in a patient are acquired. A three-dimensional surface of the first type of data representing the planar region is generated. A depth of the surface at each point in a plane representing the planar region is spaced away from the plane by an amount based on the second type of data. First and second views of the surface from first and second viewing angles are rendered. The first angle is different than the second angle. The first and second views of the surface are stereoscopically displayed.

In a second aspect, a system is provided for information layering in medical imaging. A processor is operable to generate a mesh varying in depth as a function of values from a first mode of imaging and having texture of values from a second mode of two-dimensional imaging. The processor is operable to render an image from the mesh. A display is operable to display the image.

In a third aspect, a non-transitory computer readable storage medium has stored therein data representing instructions executable by a programmed processor for information layering in medical imaging. The storage medium includes instructions for setting depth queues for a planar region as a function of one type of information, and generating a stereoscopic visualization from the depth queues and another type of information representing the planar region.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Stereoscopic or three-dimensional visualization may enhance two dimensional ultrasound data by enabling an additional layer of information using depth queues. For example, elastography information may be layered onto a B-mode with color Doppler image by representing stiff tissue as protruding from the screen. As another example, depth queues may be utilized to represent the thickness or other physical dimensions of the 2D image, such as representing elevation thickness in two-dimensional imaging. 2D imaging may be enhanced by providing visualization of the ultrasound beam shape to facilitate per voxel spatial resolution display.

Stereoscopic or three-dimensional visualization allows a display to represent both conventional 2D image information as well as other information as depth on a per-pixel basis. There are many methods for producing stereoscopic images, such as using a compatible monitor and glasses. Two images are rendered from slightly different orientations and are displayed simultaneously such that the user perceives the images as a single stereoscopic visualization. Compared with conventional adjacent display of different images, the visualization of the data representing the plane with depth based on an information layer may be more realistic and intuitive for a human observer and may be large.

Stereoscopic or three-dimensional visualization is applied to two dimensional imaging. Depth represents an additional dimension of information rather than different voxels in a volume. Depth visually represents a dimension of information other than spatial information. There may be one or more advantages to this approach compared with conventional methods of displaying the same information alongside the anatomical B-mode image. First, spatial matching of information is intuitive and more exact. Second, physical image size is not diminished for simultaneous display. Third, information fidelity, such as dynamic range, for the data is not diminished as with overlays, which typically require adding a transparency layer to at least one data source.

Figure 1:
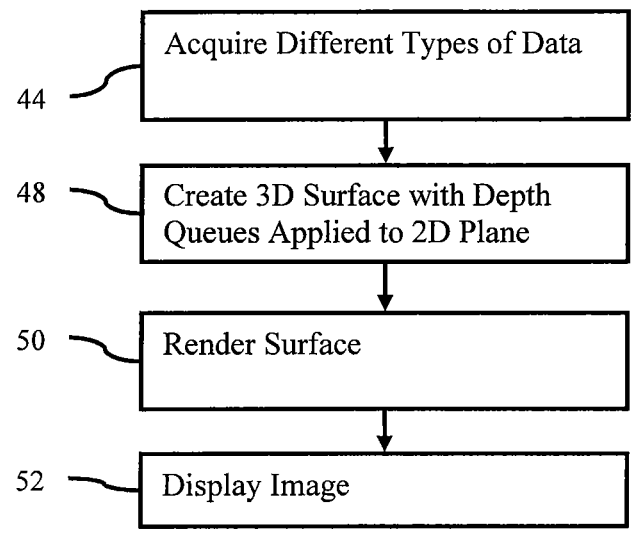
FIG. 1 is a flow chart diagram of one embodiment of a method for information layering in medical imaging.

FIG. 1 shows a method for information layering in medical diagnostic ultrasound or other medical imaging. The acts of FIG. 1 are implemented by the system 10 of FIG. 3 or a different system. The acts shown in FIG. 1 are performed in the order shown or a different order. Additional, different, or fewer acts may be performed. For example, one or more acts 44, 50, and 52 may not be used.

To begin a workflow, user configuration information is received. Signals from a user input or interface are received by a processor. The processor controls operation of the system based on preprogramming, adaptive detection, and/or the received user configuration information. The configuration is received during initial set-up of a system, during configuration for a given examination, during examination, or at other times.

Any configuration information may be received. For example, the user indicates that the system is to be used for instrument guidance or other information layering. The system may prompt further input or provide the visualization without further input.

Configuration information may include what forms of information or type of parameters are to be used for imaging. For example, the user selects between flow mode, B-mode, elasticity mode, contrast agent mode, harmonic mode, other ultrasound modes, computed tomography modes, magnetic resonance modes, or other modes. The user may select the type of information rather than the type of mode, such as vascular and stiffness information. The system maps the type of information to the corresponding mode or modes.

After configuration, the different types of data are acquired in act 44. The data is acquired by scanning a planar region. Two-dimensional imaging is performed such that data representing a plane or slab is acquired without acquiring data representing other planes (e.g., without acquiring data representing locations outside the planar region) for each given image. As the transducer or patient moves, the scanned planar region may be at a different location in the patient, but is still a scan of a single plane for a given image. In alternative embodiments, data along a plane in a scanned volume is selected, such as associated with multi-planar reconstruction. The selected data for imaging represents a planar region rather than a volume or a plurality of different planes.

To scan an internal region of a patient, body, or other structure with ultrasound, the user or a robot positions a transducer against or within the patient. Acoustic energy is generated by the transducer. Echoes from the acoustic energy are received by the transducer or a different transducer. The transducer converts the echoes to electrical signals.

Using beamforming, Fourier analysis, or other processing, the acoustic response of different locations within a scanned region is detected. Any two-dimensional scan format may be used, such as linear, sector, or Vector®. Point (e.g., spectral or continuous wave mode), line (e.g., M-mode or color M-mode), or three-dimensional scanning may be used.

Any size field of view or scan region may be used. The user positions the transducer on or in the patient in the vicinity of and directed at a target anatomy. For example, the transducer is positioned adjacent the user's torso or breast. Various samples are obtained in any sampling density from the region of interest within the field of view. The samples are from anatomical locations within the scan region, such as sampling hundreds or thousands of anatomical locations by scanning a two-dimensional region.

In alternative embodiments, the data is acquired without current scanning. For example, a stored data set is acquired by loading from memory or transfer over a network. The scan was previously performed or a data model is used to generate the data.

Two or more types of data are acquired. In one embodiment, three or more types of data are acquired. For example, data is acquired for a B-mode anatomical image using grayscale to indicate echogenicity and a color overlay representing Doppler based flow (e.g., velocity, variance, and/or power). Other types of data may be mapped to 2D grayscale and/or color. Data for stiffness (e.g., elastography), density (e.g., computed tomography data), contrast (e.g., MRI or ultrasound) or other characteristic is mapped for depth.

The different types of data represent different types of characteristics. One or more modes of ultrasound imaging are used. In one embodiment, multiple modes of ultrasound imaging are used without other types of imaging. Ultrasound-based imaging may provide a variety of types of information regarding tissue composition. Anatomical information based on acoustic impedances (B-mode), vascular flow information based on Doppler frequency shifts, and stiffness information based on measured strain (elastography) are three examples. Alternatively, the same mode is used, but with different settings, to provide two or more types of data.

In other embodiments, one or more modes of ultrasound imaging are used with one or more other types of imaging, such as using volume fusion technologies. Tissue density may be measured by computed tomography (CT). The CT information is registered spatially with the ultrasound information. Magnetic resonance may measure softness or hardness of tissue based on identification of the type of tissue or other contrast. In other embodiments, only non-ultrasound data is used.

Different imaging modes may use the same or different scans. For example, intensity or acoustic impedance is detected in B-mode imaging. For Doppler or other flow mode, multiple transmissions and corresponding receive operations for the same locations are used to estimate the velocity, variance, or power of flow (fluid) or motion (tissue). Elasticity mode scanning may be used. The stiffness of tissue is estimated. The stiffness may be estimated by detecting an amount and/or timing of tissue response to force, such as acoustic radiation force or palpitation. Tissue response to longitudinal or shear waves may be detected by correlation of scans from different times. Strain or strain rate imaging may be used for determining tissue stiffness.

In act 48, a surface is created with depth queues applied to a two-dimensional plane. Depth queues for a planar region are set as a function of one type of information. The one type of information is a single source (e.g., only elasticity data) or a combination from multiple sources (e.g., a combination of elasticity and contrast agent data).

The data for each location distorts the surface from planar. The surface begins as planar, such as a two-dimensional plane corresponding to the scanned internal plane in the patient. The magnitude or other characteristic of the data moves the surface as a mesh (e.g., depth mapping bumps the mesh away from planar), forming a surface with peaks and/or valleys. The data may be scaled or the movement limited, such as mapping the dynamic range of the data to a dynamic range of the depth queue. For each location or node in the mesh, the displacement from the plane is based on the data mapped for that location. Since different locations may be associated with different data values, the amount of deviation from the plane varies across the surface. Each location is based on the data representing the plane, such that data representing the plane is used to bump the surface away from that plane.

Figure 2:
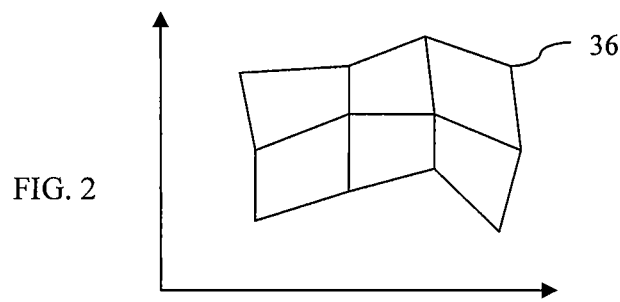
FIG. 2 is a graphical representation of a portion of an example surface.

FIG. 2 shows an example surface 36 distorted based on data. The intersections represent sample or pixel points. A depth of the surface at each point in the plane representing the planar region is spaced away from the plane by an amount based on the selected data. The selected data represents the plane before the distortion of the surface 36.

The distorted mesh or created three-dimensional surface may be used without further processing. Alternatively, the surface is filtered. For example, two-dimensional low pass filtering may be applied. Rather than filtering the surface, the data may be filtered prior to creating the surface.

Any type of information may be mapped to the depth. For example, tissue stiffness derived from elastographic imaging techniques modulates the depth dimension for visualization simultaneously with B-mode and color Doppler information on a single image. Other types of information that may be mapped onto depth include density information derived from spatially registered computed tomography, positron emission tomography based metabolic activity information, or contrast enhancement information. B-mode, Doppler mode, or any other medical imaging mode may be used for mapping depth. In one embodiment, the type of information mapped to depth is ultrasound stiffness, density, or contrast agent mode.

In an alternative embodiment, the type of information mapped to depth is model data or other data not representing the tissue or fluid in the patient. For example, data modeling an ultrasound beam shape is mapped to depth. The ultrasound beam shape may be visualized. The width in elevation of the beams used for scanning is modeled. For each location, the beam thickness associated with the data is mapped. Different ranges may have different elevation thickness based on the focus. This different thickness is mapped from the model, providing a surface with a generally hour-glass shape in range and level in azimuth. The 3D model or object representing the shape of the ultrasound beam for the current set of parameters (e.g., transducer, focus, and depth/range) is used to alter the mesh. This allows the user to quickly evaluate actual voxel dimensions (spatial resolution) throughout the image, and thus account for partial volume effects during image interpretation. For example, deep tissues are typically imaged with lower effective spatial resolution than shallow tissues.

The surface shape is created by mapping the information to depth (e.g., altering the depth for the surface from a plane based on the information). The values represented by each point on the surface are from one or more different sources.

The variable surface is used to display two-dimensional image data. The three-dimensional surface is textured with one or more types of data where the depth is a function of another type of data. The same data used for depth of the surface may also be used for texturing or is only used for modulating depth. The two-dimensional image data is laid on the surface. For example, the value at a given x, y location is based on the B-mode and/or Doppler mode data (e.g., a B-mode scalar value of 120 out of 256 levels or a Doppler mode color value) while the depth at the x,y location is based on other data. Each location or node of the mesh has a value assigned based on the data for that location in the two-dimensional plane. By mapping the two-dimensional image data over the three-dimensional surface, information about multiple types of data is indicated for two-dimensional imaging or scanning.

The resulting three-dimensional surface is rendered in act 50. In one embodiment, the surface is rendered from one view. The user may change the view angle for other renderings of the surface. A sequence of surfaces may be rendered. As data is acquired in act 44 for a new scan of the same or different plane, a new surface is generated and rendered. The rendering generates an image of the three-dimensional surface for the two-dimensional display device.

In one embodiment, the surface is rendered a plurality of times. For example, a sequence may be rendered from one static surface, such as to render views from different angles for a rotating perspective display. As another example, stereoscopic viewing is provided. Different views of the surface are rendered from different viewing angles. The angles are slightly offset, such as associated with a user viewing from different eyes (e.g., offset by 1-20 degrees or less than 10 degrees different). A stereoscopic visualization is generated from the surface. For example, a stereoscopic visualization is generated from ultrasound B-mode, Doppler mode, or B-mode and Doppler mode information with depth mapped to another source. The stereoscopic visualization may allow the user to better appreciate the depth coding of the surface.

For stereoscopic viewing, the imaging system renders different three-dimensional representations. The three-dimensional representations are of the same surface at a same or substantially same time. For example, two different viewing directions are used with the same set of surface data for rendering different three-dimensional representations for left and right eye stereo viewing. The rendering is performed once or is continuous in an ongoing process, such as rendering additional views from the same two viewing angles or different pairs of viewing angles as a function of time from more recently acquired data. More than two renderings may be provided for a same set of data, such as generating renderings from different directions or user perspectives for a same scan. The renderer may render the left and right view with half the vertical resolution to speed up the operation.

Any type of rendering may be used. For example, surface rendering is used. Projection rendering may be used. Lighting, shading, or other rendering processes may be used.

In act 52, the rendered view or views are displayed. For example, a three-dimensional rendering of the surface is displayed as an image. As another example, two views of the surface are stereoscopically displayed. By displaying the rendered view or views, depth is indicated to a viewer.

The generated image is an ultrasound image, such as a combination of two or more of B-mode image, Doppler image, elasticity image, or contrast agent image. Data from non-ultrasound sources may be used. The data acquired by the scanning of act 44 is used to generate the image. The image represents the anatomical structure in the planar internal region, but with depth mapped to one or more sources of data rather than data at different elevations.

For stereoscopic display, two different three-dimensional representations are displayed in stereo or substantially simultaneously for a given time or substantially same time which allows for sequential display, but at a rate for providing stereoscopic viewing. For real time imaging, a sequence of pairs or stereo views are rendered and used to generate stereoscopic display. The stereo representations are provided as sequential images or images generated at a same time.

Stereoscopic views are generated using auto stereoscopic methods or methods using an additional apparatus, such as displaying the stereoscopic images on head mounted displays. As another example, sequentially generated representations or stereo views are stereoscopically displayed by viewing the representations through different polarization, switchable shutters or both polarization and shuttering. For shutter glasses, exposure of each representation to selected eyes is performed in synchronization with the generation of the corresponding images. By quickly alternating between left eye access to a left eye view and right eye access to a right eye view, a stereoscopic view or display is created. As an alternative to shutter glasses, glasses with polarization, or glasses with different color filtering mechanisms may be provided. The different views are generated with different polarization or color. By using polarizing lens in combination with the switching of a polarizing panel or other display, the different representations sequentially generated on the display are provided to different eyes of the viewer. By generating the images sequentially, such as at over 100 Hertz, a three-dimensional stereoscopic view with minimal blur, flicker, interference or undesired imaging effects is provided.

As an alternative to sequential generation of the different views, the different views or three-dimensional representations are output at a same or substantially same time. Two different displays of the two different representations are generated at the same time, such as generating the images on LCD displays or projectors on glasses limiting exposure of each of the images to a particular eye.

The same representations may be generated a plurality of times for viewing by a plurality of different users, such as generating the same representations on different LCD displays mounted on individual glasses. Alternatively, stereoscopic display is generated for a plurality of people at the same time using the same monitor or monitors. Each of the different viewers or users has associated glasses, head mounted displays or other additional apparatus for viewing the sequentially or parallel generated images stereoscopically. In yet another embodiment, multiple users view a same monitor capable of generating a three-dimensional view, such as a multilayer LCD screen.

The image is a static image. In an alternative embodiment, the image is part of an ongoing sequence of images generated in real-time with the scanning. The scanning, creating of the surface, rendering, and displaying of acts 44, 48, 50, and 52 are repeated while the scanning is occurring. Within seconds of scanning, such as while scanning for a next image, the image is generated. The image is replaced as soon as the next image is available, such as every $\frac{1}{30}^{th}$ of a second. As the transducer, target region, or patient move or change position (i.e., position of the target relative to the transducer changes), subsequent images adapt, creating a new surface by altering the depths of the surface and/or altering the surface texture.

Figure 3:
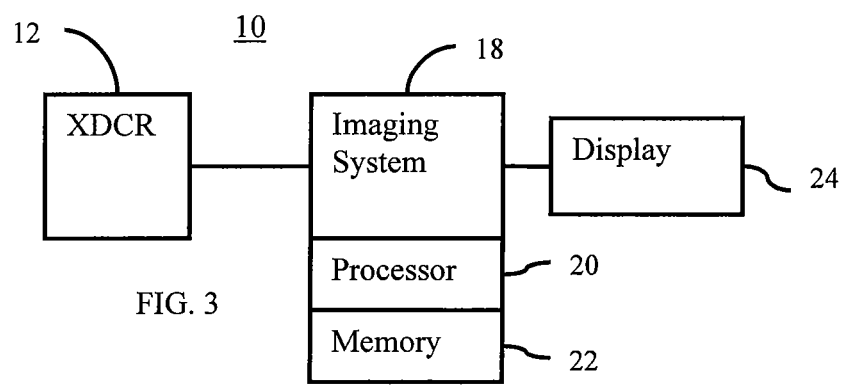
FIG. 3 is a block diagram of one embodiment of a system for information layering in medical imaging.

FIG. 3 shows a system 10 for information layering in medical imaging. In one embodiment, the system 10 is a medical diagnostic ultrasound imaging system, so includes a transducer 12, an imaging system 18, a processor 20, a memory 22, and a display 24. Additional, different, or fewer components may be provided. For example, the system 10 includes a user interface, or does not include the transducer 12. In one embodiment, the system 10 is a medical diagnostic ultrasound imaging system. In other embodiments, the processor 20 and/or memory 22 are part of a workstation or computer different or separate from the imaging system 18 and/or transducer 12. The workstation is adjacent to or remote from the imaging system 18. In yet other embodiments, the transducer 12 is not provided and the system is a CT, MRI, or other imaging system.

The transducer 12 is a single element transducer, a linear array, a curved linear array, a phased array, a 1.5 dimensional array, a two-dimensional array, a radial array, an annular array, a multidimensional array, a wobbler, or other now known or later developed array of elements. The elements are piezoelectric or capacitive materials or structures. In one embodiment, the transducer 12 is adapted for use external to the patient, such as including a hand held housing or a housing for mounting to an external structure.

The transducer 12 converts between electrical signals and acoustic energy for scanning a region of the patient body. The region of the body scanned is a function of the type of transducer array and position of the transducer 12 relative to the patient. For example, a linear transducer array may scan a rectangular or square, planar region of the body. As another example, a curved linear array may scan a pie shaped planar region of the body. Scans conforming to other geometrical regions or shapes within the body may be used, such as Vector® scans. The scans are of a two-dimensional plane. Different planes may be scanned by moving the transducer 12, such as by rotation, rocking, and/or translation. Alternatively, a volume is scanned. The volume is scanned by electronic steering alone (e.g., volume scan with a two-dimensional array) or mechanical and electrical steering (e.g., a wobbler array or movement of an array for planar scanning to scan different planes).

The imaging system 18 is a medical diagnostic ultrasound system. For example, the imaging system 18 includes a transmit beamformer, a receive beamformer, a detector (e.g., B-mode, elasticity, and/or Doppler), a scan converter, and the display 24 or a different display. The imaging system 18 connects with the transducer 12, such as through a releasable connector. Transmit signals are generated and provided to the transducer 12. Responsive electrical signals are received from the transducer 12 and processed by the imaging system 18. The imaging system 18 causes a scan of an internal region of a patient with the transducer 12 and generates data representing the region as a function of the scanning. The data is beamformer channel data, beamformed data, detected data, scan converted data, and/or display data. The data represents anatomy of the region. For each point in the internal region or sub-sampled locations, data for each of the different types of ultrasound modes of scanning is acquired. For example, tissue stiffness and fluid imaging data are acquired.

In another embodiment, the imaging system 18 is a workstation or computer for processing ultrasound or other medical data. Ultrasound data is acquired using an imaging system connected with the transducer 12 or using an integrated transducer 12 and imaging system. The data at any level of processing (e.g., radio frequency data (e.g., I/Q data), beamformed data, detected data, and/or scan converted data) is output or stored. For example, the data is output to a data archival system or output on a network to an adjacent or remote workstation. The imaging system 18 processes the data further for analysis, diagnosis, and/or display. In other embodiments, the imaging system is a CT or MRI imaging system.

The processor 20 is one or more general processors, digital signal processors, graphic processing unit (GPU), graphics card, application specific integrated circuits, field programmable gate arrays, controllers, analog circuits, digital circuits, server, combinations thereof, network, or other logic devices for creating, rendering, and/or displaying a three-dimensional surface. A single device is used, but parallel or sequential distributed processing may be used. In one embodiment, the processor 20 is a system controller or other processor of the imaging system 18 for generating the mesh and a GPU for rendering the mesh. In another embodiment, the processor 20 is or includes a video processing unit operable to output multiple three-dimensional representations of a same region at different viewing angles. For example, the CPU in conjunction with a graphics card using open GL drivers or other drivers generates different views of the three-dimensional surface to simulate left and right eye viewing angles. The different representations represent the region at a substantially same time from different viewing perspectives, such as associated with a left eye and a right eye, for stereoscopic display.

The processor 20 generates a mesh. The mesh represents sample locations, such as pixel locations or polar coordinate scan locations, in a plane. Values from one or more imaging modes are provided for the various locations or points in the plane. For a given mesh even after depth mapping, the mesh and associated values do not represent points outside of the plane.

The depth (e.g., height or spacing away from planar) of the mesh is varied based on values from one or more modes of imaging. The mesh is a three-dimensional structure based on data representing the plane. The depth dimension is mapped from values. Any mapping function may be used. Greater or lesser values are mapped to greater or lesser deviations from planar. The mesh is formed from the points in the plane where the depth away from the plane of each of the points is based on the value from the one or more modes of imaging at the respective point. Where the values vary across space, the depth varies across the mesh.

The mode or modes mapped to depth may be any imaging data. For example, the mode of imaging is stiffness (e.g., strain or elasticity), density, or contrast agent mode. The data for depth is obtained from ultrasound data, CT data, and/or MRI data. In alternative embodiments, model data or other information is used to determine the depth or variation along one or more axes of the mesh.

Another mode or modes are displayed as a texture on the mesh. The gray scale, color, hue, brightness, transparency, or other pixel characteristic is mapped to the data, such as for two-dimensional imaging. For example, the texture of the mesh is values from a combined ultrasound B-mode and Doppler mode data. Each location on the mesh is either a B-mode value, Doppler value, or both. The two-dimensional scan data is warped to fit the three-dimensional surface despite representing only the scan plane.

The processor 20 is operable to render an image from the mesh. Three-dimensional rendering is performed to preserve the depth information. The rendering is of the texture such that a planar region in the patient is represented as three-dimensional. The processor 20 or the user may cause a given mesh to be rendered in sequence from different viewing angles, increasing the visualization of the depth information as well as the texture.

In other embodiments, the processor 20 renders the image from the mesh at different angles such that the image indicates the depth to a viewer in stereo. By accounting for left and right eye positions, two different viewing angles may be defined for a same mesh or three-dimensional surface. Different three-dimensional representations are rendered as a function of the same data and correspond to the different viewing angles.

For stereo viewing, the processor 20 outputs three-dimensional representations associated with the two different viewing angles substantially simultaneously in parallel or sequence. As the user position alters with respect to the scan plane or mesh, one or both viewing angles change. With or without movement of the user's perspective, a continuing sequence of three-dimensional representations may be rendered for real time imaging. For sequential output, the representations associated with each of the viewing angles is output in pairs or other groupings to provide the views for each of the viewing angles at substantially the same time. The output rate for each viewing angle or for both viewing angles is synchronized with the video processing unit, the image frame display rate or combinations thereof.

In one embodiment, the system 10 provides the stereoscopic viewing without monoscopic viewing. Alternatively, the processor 12 is operable in both stereoscopic and monoscopic modes. The mode of operation is selected by a user or defaults to a given mode, such as defaulting to stereoscopic viewing when a stereoscopic viewing device is attached to the ultrasound imaging system 18. For monoscopic operation, the circuitry used for stereoscopic operation is bypassed.

The processor 20 outputs image data. The image data may be data at any stage of processing, such as prior to or after detection. The image data may be specifically formatted for display, such as red, green, blue (RGB) data. The image data may be prior to or after any mapping, such as gray scale or color mapping.

The processor 20 operates in a static mode, such as rendering one or more images based on one mesh. Alternatively, the processor 20 operates in an ongoing basis or in real-time with sequential scanning. The image data is output as the internal region changes during examination. The change is due to transducer movement or patient movement. As new data for the texture and/or depth becomes available, the new data is used for creating an updated or different mesh and rendering a corresponding image. The image data is output in real-time with the scanning during examination of the patient. A sequence of images is generated, each new image replacing a recent image. The mesh is displayed in each new image.

The memory 22 stores the data from the different scans, the mesh, and/or the output image data. Alternatively or additionally, the memory 22 is a computer readable storage medium with processing instructions. Data representing instructions executable by the programmed processor 20 is provided for information layering in medical imaging. The instructions for implementing the processes, methods, acts, and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 24 is a CRT, LCD, projector, plasma, printer, or other display for displaying two-dimensional images or three-dimensional representations. The display 20 displays ultrasound or other images as a function of the output image data. For example, a rendering of the mesh is generated. The image has color, hue, and/or brightness at each pixel based on one or more types of information. The image is rendered to show depth. For example, light modeling (e.g., Gouraud shading) of a surface rendering indicates depth. The depth information is based on one or more others types of information.

Depth may be shown by displaying a sequence of views with rotation from different perspectives. The human brain can construct 3D information if motion is present for a 2D image. An automatic animation of a single image for each given time, such as sweeping through a plurality of viewing angles as a function of time, allows a user to perceive the series of three dimensional representations as having depth. The animation is of a single mesh, not a real-time scanning or a cine loop playback.

In one embodiment, the display 24 is a stereoscopic display. The stereoscopic display is operable to display three-dimensional representations from two or more views substantially simultaneously. The display 14 sequentially displays different representations or displays the different representations in parallel.

The principle of how humans see stereo image is well understood. Each eye produces a flat 2D retinal image. The brain constructs a stereo or 3D image using both images. The slight viewing angle difference (ocular parallax) is the primary factor that the brain uses to construct the stereo image. The stereo display 14 is based on the principle of display the left representation to the left eye and the right representation to the right eye. Two approaches or general categories of stereoscopic displays are auto stereoscopic viewing and stereoscopic with a viewing apparatus.

Autostereoscopic displays include holograms, volumetric display (e.g., multiple layer LCDs) and directional projection (e.g., projection of images to each eye). Other autostereoscopic displays are free-viewing using a fixed focus, lenticular devices, parallax barriers (e.g., prisms), parallax illumination or a moving slit to alternately block left and right eye viewing. The autostereoscopic method may not require the use of any extra viewing apparatus, such as glasses. Autostereoscopic displays may use hardware to produce satisfactory results for multiple viewers.

Other stereoscopic displays include a stereoscope, head-mounted display device (e.g., LCD glasses or glasses with projectors), anaglyph (e.g., color coded glasses or viewing), polarized (e.g., spatially multiplexed or field-sequential), or sequential viewing (e.g., shutter glasses). These stereoscopic displays may include a monitor, such as a CRT, LCD or projector, and an additional device, such as glasses, another monitor, or another device to interact with the monitor to provide stereoscopic viewing. The monitor is a display device spaced from the additional device, such as monitor or screen spaced from a head mounted device. The monitor displays the first and second three-dimensional representations in sequence, such as for left and right eye sequential viewing. The display is in conjunction with operation of the additional or head mounted device. Alternative stereoscopic displays now known or later developed may be used, such as motion parallax or Pulfrich effect viewing devices.

The additional device may be personal to each viewing or may operate for multiple viewers. For example, the additional device of the stereoscopic display is a head mounted device, such as a helmet and visor or glasses. In one embodiment, a head mounted display or monitor is used, such as glasses with two LCD monitors on the glasses to provide the left and right eye representations to an individual viewer. In other embodiments, the head mounted device operates in conjunction with the monitor to provide a stereoscopic display of a region. For example, stereoscopic image pairs are displayed in sequence on the monitor for viewing through the additional device, such as shutter glasses or polarized glasses. A wired or wireless connection is used to control operation of the additional device in conjunction with the monitor.

The polarization method uses lenses or glasses that have different polarization for the left and right eye. The monitor outputs the different representations or views with polarized light matched to the appropriate eye. For example, the monitor is a switching polarizing panel or monitor that sequentially alters between different polarizations for the different 3D representations.

The field sequential method uses shutters to limit exposure to the left and right eyes in sequence with the sequential display of different 3D representations. The monitor outputs the different views in sequence at the original or input refresh rate (e.g., 60 Hz per eye or 120 Hz for all images). The additional device, such as shutter glasses, operates in sequence with the display on the monitor. For example, liquid crystal lenses alternate between opaque and transparent. An analog or digital controller is provided in the glasses to synchronize the left or right eye viewing with the display screen. The left eye is transparent and the right eye is opaque for 3D representations for the left eye, and the right eye is transparent and the left eye is opaque for 3D representations for the right eye.

A user interface may be provided, such as a keyboard, trackball, mouse, or other input device and the display 24. The user interface is operable to receive user indication of a type of data, such as the information layers to be used and which to map to depth.

The processor, system or other components are operable to perform various acts. Hardware, software, or combinations thereof provide the instructions for performing the acts. The processor, system, or other components may be configured by having the software, hardware, or combinations thereof.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for information layering in medical diagnostic ultrasound, the method comprising:
   acquiring at least first and second types of data both representing different types of characteristics of a planar region in a patient, the first and second types of data acquired as two-dimensional ultrasound imaging data for the planar region without acquiring additional data of the first and second types of data representing locations outside the planar region for stereoscopic first and second views;
   generating a three-dimensional surface of the first type of data representing the planar region where a depth of the surface at each point in a plane representing the planar region is spaced away from the plane by an amount based on the second type of data only from the planar region;
   rendering the first and second views of the surface from first and second viewing angles, the first angle different than the second angle; and
   stereoscopically displaying the first and second views of the surface.

2. The method of claim 1 wherein acquiring comprises scanning the planar region and wherein the first and second types of data comprise B-mode and stiffness, density, or contrast mode data.

3. The method of claim 1 wherein acquiring comprises acquiring a third type of data, the three-dimensional surface being of the first and third types of data.

4. The method of claim 3 wherein acquiring comprises acquiring B-mode data as the first type of data, Doppler or flow mode data as the third type of data, and elasticity or contrast agent mode data as the second type of data.

5. The method of claim 1 wherein generating comprises determining the amount for each of the points from a magnitude of the data of the second type for the respective point such that the depth away from the plane varies across the surface as a function of the second type of data.

6. The method of claim 1 wherein rendering comprises three-dimensional rendering of the three-dimensional surface such that the planar region is represented as three-dimensional.

7. The method of claim 1 wherein rendering comprises surface rendering with the first angle less than 10 degrees different than the second angle.

8. The method of claim 1 wherein stereoscopically displaying comprises displaying the first and second views such that the depth is indicated to a viewer.

9. A method for information layering in medical diagnostic ultrasound, the method comprising:
- acquiring at least first and second types of data both representing different types of characteristics of a planar region in a patient;
- generating a three-dimensional surface of the first type of data representing the planar region where a depth of the surface at each point in a plane representing the planar region is spaced away from the plane by an amount based on the second type of data only from the planar region, wherein generating comprises texturing the three-dimensional surface with the first type of data where only the depth is a function of the second type of data;
- rendering first and second views of the surface from first and second viewing angles, the first angle different from the second angle; and
- stereoscopically displaying the first and second views of the surface.

10. A system for information layering in medical imaging, the system comprising:
- a processor configured to generate a three-dimensional mesh varying in depth as a function of values from a first mode of imaging and having texture on the three-dimensional mesh of values representing just a plane from a second mode of two-dimensional imaging and configured to render an image from the three-dimensional mesh, wherein the values of the first and second modes represent different points in the plane and not points outside the plane, the mesh formed from the points in the plane where the depth away from the plane of each of the points is based on the value from the first mode at the respective point such that the depth varies across the mesh; and
- a display operable to display the image.

11. The system of claim 10 wherein the first mode of imaging comprises stiffness, density, or contrast agent mode data.

12. The system of claim 11 wherein the texture comprises values from an ultrasound B-mode and an ultrasound Doppler mode.

13. The system of claim 10 wherein the processor and display comprise an ultrasound imaging system.

14. The system of claim 10 wherein the processor is operable to three-dimensionally render the texture such that a planar region in the patient is represented as three-dimensional.

15. The system of claim 10 wherein the display comprises a stereoscopic display, the processor configured to render the image from the mesh at different angles such that the image indicates the depth to a viewer.

16. In a non-transitory computer readable storage medium having stored therein data representing instructions executable by a programmed processor for information layering in medical imaging, the storage medium comprising instructions for:
- setting depth queues with depth being in a direction outside of a planar region for locations in the planar region as a function of one type of information representing just the planar region, the one type of information comprising two-dimensional ultrasound imaging data for the planar region without additional data representing locations outside the planar region; and
- generating a stereoscopic visualization from the depth queues and another type of information representing the planar region, the stereoscopic visualization being of the planar region.

17. The non-transitory computer readable storage medium of claim 16 wherein the one type of information comprises an ultrasound beam shape and wherein the other type of information comprises ultrasound B-mode, Doppler mode, or B-mode and Doppler mode information.

18. The non-transitory computer readable storage medium of claim 16 wherein the one type of information comprises an ultrasound stiffness, density, or contrast agent mode and wherein the other type of information comprises ultrasound B-mode, Doppler mode, or B-mode and Doppler mode information.

* * * * *